US005641808A

United States Patent [19]
Gaffney et al.

[11] Patent Number: 5,641,808
[45] Date of Patent: Jun. 24, 1997

[54] SYNERGISTIC ANTIMICROBIAL COMPOSITION OF 1,2-DIBROMO-2,4-DICYANOBUTANE AND ESTERS OF PARAHYDROXYBENZOIC ACID

[75] Inventors: Tammy W. Gaffney; Edwin R. Tefft, both of Pittsburgh, Pa.

[73] Assignee: Calgon Corporation, Pittsburgh, Pa.

[21] Appl. No.: 523,097

[22] Filed: Sep. 1, 1995

[51] Int. Cl.$^6$ .......... A01N 33/00; A01N 37/00; A01N 37/10; A01N 37/34
[52] U.S. Cl. .......... 514/526; 504/157; 504/158; 514/544
[58] Field of Search .......... 514/526, 544; 504/157, 158

[56] References Cited

U.S. PATENT DOCUMENTS

| | | | |
|---|---|---|---|
| 3,644,380 | 2/1972 | Harmetz et al. | 260/294.9 |
| 3,833,731 | 9/1974 | Grier et al. | 424/300 |
| 3,833,743 | 9/1974 | Morse et al. | 424/195 |
| 3,873,597 | 3/1975 | Harmetz et al. | 260/465.7 |
| 3,877,922 | 4/1975 | Grier et al. | 71/67 |
| 3,929,858 | 12/1975 | Swigert | 260/465.7 |
| 4,442,122 | 4/1984 | Engelhart et al. | 424/304 |
| 4,496,581 | 1/1985 | Engelhart et al. | 514/438 |
| 4,830,657 | 5/1989 | Jakubowski et al. | 71/67 |
| 5,034,405 | 7/1991 | Jakubowski | 514/369 |
| 5,124,355 | 6/1992 | Tully et al. | 514/526 |
| 5,364,874 | 11/1994 | Morpeth | 514/373 |
| 5,441,979 | 8/1995 | Oppong et al. | 514/515 |
| 5,444,088 | 8/1995 | Syrinek | 514/526 |

OTHER PUBLICATIONS

Orth, *Handbook Of Cosmetic Microbiology*, pp. 88–91 (1993).
Steinberg, *Cosmetics & Toiletries*, vol. 107, pp. 77–78, 80, 82 (1992).
*Cosmetics & Toiletries*, vol. 108, pp. 47–48 (1993).

*Primary Examiner*—Allen J. Robinson
*Attorney, Agent, or Firm*—D. R. Meyers; W. C. Mitchell

[57] ABSTRACT

Synergistic antimicrobial combinations comprising 1,2-dibromo-2,4-dicyanobutane and at least one ester of parahydroxybenzoic acid are disclosed. Methods for using these synergistic combinations to inhibit microbial growth are also disclosed.

10 Claims, No Drawings

SYNERGISTIC ANTIMICROBIAL COMPOSITION OF 1,2-DIBROMO-2,4-DICYANOBUTANE AND ESTERS OF PARAHYDROXYBENZOIC ACID

BACKGROUND OF THE INVENTION

1. Field of the Invention

The present invention relates to synergistic antimicrobial compositions which are generally useful for inhibiting microbial growth wherever such microbial growth is found, e.g. in aqueous systems related to a wide variety of industrial applications. More particularly, the present invention relates to synergistic antimicrobial compositions of 1,2-dibromo-2,4-dicyanobutane (DBDCB) and at least one of the esters of parahydroxybenzoic acid. Methods for using the same are also disclosed.

2. Description of the Background Art

Both 1,2-dibromo-2,4-dicyanobutane (DBDCB), also known as 2-bromo-2-bromomethylglutaronitrile, and esters of parahydroxybenzoic acid, also known as parabens, are known individually as antimicrobial agents. The unexpected finding of the present invention is that they are synergistic when used in combination. As used herein, the terms "synergy" and "synergistic" refer to instances where the effectiveness of a composition comprising two or more biocides, such as DBDCB and at least one paraben, exceeds the sum of the efficacies of the individual components taken alone. Thus, using a synergistic biocidal combination may allow for use of a lower overall concentration of biocide or the realization of an enhanced antimicrobial effect at a comparable dosage.

U.S. Pat. Nos. 3,833,731, 3,877,922, 3,873,597, 3,644,380, 3,833,743, and 3,929,858 disclose DBDCB and its use as an antibacterial, antifungal, and algicidal agent. Compounds related to DBDCB are also effective as antimicrobial agents. For example, U.S. Pat. No. 4,442,122 describes the use of 1,2-dibromo-2-cycloalkane compounds to inhibit microbial growth, and U.S. Pat. No. 4,496,581 discloses 1,2-dibromo-2-cyano-2-(heterocyclic) alkane compounds and their use as antimicrobial agents.

The use of DBDCB and related compounds in conjunction with other antimicrobial agents is also known in the art. U.S. Pat. No. 4,830,657 describes a synergistic antimicrobial combination comprising DBDCB and 1,2-benzisothiazolin-3-one. U.S. Pat. No. 5,034,405 discloses use of admixtures of DBDCB, 2-methyl-4-isothiazolin-3-one and 5-chloro-2-methyl-4-isothiazolin-3-one as antimicrobial agents. U.S. Pat. No. 5,124,355 discloses an antimicrobial composition of DBDCB and 2-(decylthio) ethaneamine and a method of using the same. U.S. Pat. No. 5,364,874 discloses the antibacterial and antifungal activity of a biocidal combination containing 2-halo-2-halomethylglutaronitriles, including DBDCB, and 4,5-polymethylene-4-isothiazolin-3-one.

Likewise, esters of parahydroxybenzoic acid ("parabens") are known for their antimicrobial properties. For example, parabens are known as preservatives for cosmetic products, food products and pharmaceutical preparations. See, e.g., Orth, *Handbook of Cosmetic Microbiology*, p.88–91 (1993) (discussing the use of parabens as preservatives in cosmetic products, drugs and food); Steinberg, *Cosmetics & Toiletries*, 107, 77–78, 80, 82 (1992) (discussing use of parabens as cosmetic preservatives, both alone and in combination with other preservatives); and *Cosmetics & Toiletries*, 108, 47–48 (1993) (discussing the use of parabens as frequently used preservatives).

As used herein, the phrases "antimicrobial", "biocide", and "inhibiting microbial growth" refer to agents useful for the killing of, inhibition of, or the control of the growth of bacteria, yeast, fungi, and/or algae. A number of important industries have experienced serious adverse effects from the activity of such biological growth on the raw materials which they employ, in their process waters, on various components of their manufacturing processes, and in the finished products which they produce. Such industries include the paint, wood, textile, cosmetic, leather, tobacco, fur, rope, paper, pulp, plastics, fuel, oil, rubber, and machine industries.

It is contemplated that the synergistic admixtures of DBDCB and parabens disclosed herein, and the methods for using the same, will be useful in virtually any aqueous systems or on any article of manufacture in which inhibition of microbial growth is desired, absent compatibility problems. Important applications of the synergistic antimicrobial combinations of the present invention include, for example: inhibiting the growth of bacteria and fungi in aqueous paints, adhesives, latex emulsions, and joint cements; preserving wood; preserving cutting oils; controlling slime-producing bacteria and fungi in pulp and paper mills and cooling towers; as a spray or dip treatment for textiles and leather to prevent mold growth; as a component of anti-fouling paints to prevent adherence of fouling organisms; protecting paint films, especially exterior paints, from attack from fungi which occurs during weathering of the paint film; protecting processing equipment from slime deposits during manufacture of cane and beet sugar; preventing microorganism buildup and deposits in air washer or scrubber systems and in industrial fresh water supply systems; controlling microorganism contamination and deposits in oil field drilling fluids and muds, and in secondary petroleum recovery processes; preventing bacterial and fungal growth in paper coating processes which might adversely affect the quality of the paper coating; controlling bacterial and fungal growth and deposits during the manufacture of various specialty boards, e.g., cardboard and particle board; preventing sap stain discoloration on freshly cut wood of various kinds; controlling bacterial and fungal growth in clay and pigment slurries of various types which are manufactured for later use in paper coating and paint manufacturing and which are susceptible to degradation by microorganisms during storage and transport; as a hard surface disinfectant to prevent growth of bacteria and fungi on walls, floors, etc.; in swimming pools to prevent algal growth; and to control bacterial and fungal growth in various cosmetic products.

The synergistic antimicrobial compositions disclosed in the present invention are particularly applicable to slime control in papermaking processes. The control of bacteria and fungi in pulp and paper mill water systems which contain aqueous dispersions of papermaking fibers in various consistencies is especially important. The uncontrolled buildup of slime produced by the accumulation of bacteria and fungi causes off-grade production, decreased production due to down-time and greater cleanup frequency, increased raw material usage, and increased maintenance costs. The problem of slime deposits is especially critical in light of the widespread use of closed white water systems in the paper industry.

Another important area in which the antimicrobial compositions of the present invention are particularly useful is in the control of bacterial and fungal growth in clay and pigment slurries. These slurries comprise various clays (e.g., kaolin) and pigments (e.g., calcium carbonate and titanium dioxide) and usually are manufactured at a location separate from the end use application. This means that they are generally transported and stored for later use at the application site. Because of high quality standards for the paper and paint products in which such slurries are used, it is essential that these clay or pigment slurries have a very low microorganism count.

In addition, the synergistic combinations of the present invention and methods of using the same have been found especially useful in controlling the harmful effects of microorganisms in water or aqueous media. Systems which utilize circulating water or aqueous media become infected with microorganisms and experience substantial impairment of their efficiency when deposits of the microorganisms build up in the system. The deposits coat the walls of tanks and other vessels and any machinery or processing equipment which is employed and create blockages in pipes and valves. The deposits also create discolorations and other imperfections in the products being produced, forcing costly shutdowns. Control of microorganisms in aqueous media is particularly important where there are dispersed particles or fines in the aqueous media, e.g., dispersed cellulosic fibers and dispersed fillers and pigments in papermaking, and dispersed pigments in paint manufacture.

Accordingly, there remains a very real and substantial need for antimicrobial compositions capable of effectively controlling and/or inhibiting microbial growth in industrial aqueous systems and in articles of manufacture. Because of increasing environmental regulations, there is still a further need to provide biocidal compositions having enhanced antimicrobial effect which are effective in lower doses than historically used. Use of lower amounts of biocides has a favorable impact on the environment, and allows users to realize significant cost savings.

SUMMARY OF THE INVENTION

The present invention generally meets the above described needs by providing synergistic antimicrobial combinations comprising 1,2-dibromo-2,4-dicyanobutane (DBDCB) and at least one of the esters of parahydroxybenzoic acid (parabens). The present invention also provides a method for inhibiting microbial growth in aqueous systems and on articles of manufacture prone to such growth comprising adding to said systems or applying to said articles an effective amount of a DBDCB and parabens composition.

As used herein, the term "effective amount" refers to that amount of a composition comprising DBDCB and at least one paraben necessary to achieve the desired level of inhibition or control of microbial growth in the aqueous system or on the article being treated.

DESCRIPTION OF THE INVENTION

The present invention is directed to a synergistic antimicrobial composition comprising: a) 1,2-dibromo-2,4-dicyanobutane (DBDCB); and b) at least one ester of parahydroxybenzoic acid (parabens) wherein the weight of a) to b), on an active basis, ranges from about 1000:1 and 1:1000. As used herein, the terms "paraben" or "parabens" refer generally to methyl paraben, ethyl paraben, propyl paraben, butyl paraben, isobutyl paraben, isopropyl paraben, and benzyl paraben. According to the present invention, one or all of these parabens can be used with DBDCB to form a synergistic antimicrobial composition. The present invention is further directed to a method for inhibiting microbial growth in an aqueous system or on an article of manufacture prone to such growth, which method comprises treating said system or said article with an effective amount of an antimicrobial combination of: a) DBDCB; and b) at least one paraben, wherein the weight ratio of a) to b), on an active basis, ranges from about 1000:1 to 1:1000.

In accordance with the present invention, the weight ratios of the two components of the synergistic combination are dictated by the dosage levels of each component which demonstrate synergism, based on 100% active ingredient, relative to each end use application. Typically, the weight ratio of component a), DBDCB, and component b), at least one paraben, ranges from about 1000:1 to 1:1000 on an active basis, preferably from about 100:1 to 1:100, more preferably from about 12:1 to 1:20. As will be understood by one skilled in the art, however, the synergistic weight ratio of the two components generally varies to some extent depending on the application and the organism being controlled. For example, a higher ratio of DBDCB to parabens might be more effective in one application, while a higher ratio of parabens to DBDCB might be more effective in another application. The present DBDCB/paraben(s) compositions have been found particularly effective against bacteria when used in a weight ratio of between about 12:1 and 1:20, against yeast when used in a weight ratio of between about 2:1 and 1:10, and against mold when used in a weight ratio of between about 8:1 and 1:5.

An effective amount of a synergistic combination of DBDCB and at least one paraben should be added to the aqueous system being treated. Those skilled in the art will recognize that the required effective concentration will vary with particular organisms and in particular applications. In general, however, effective fungicidal, bactericidal and algicidal response is obtained when at least about 1 part per million (ppm) of the synergistic antimicrobial combination is employed, and preferably when these compositions are employed in concentrations ranging between about 1 and about 2000 parts per million (ppm) of the combination.

For latex paints, latex emulsions and adhesives, aqueous clay and pigment slurries, at least about 10 ppm, based on the weight of water in the product being treated, of the synergistic combination described above should generally be added. Preferably, between about 50 ppm and 2000 ppm, based on the weight of water in the product being treated, should be added. More preferable, from about 100 ppm to about 1000 ppm should be added.

For treatment of aqueous industrial systems including pulp and paper mills and water treatment systems, at least 5 parts per million (ppm), based on the weight of water in the system being treated, of the synergistic combination described above should be added. Preferably, between about 25 ppm and 200 ppm, based on the weight of water in the system being treated, should be added. More preferably, from about 100 ppm to about 150 ppm, based on the weight of water in the system being treated, should be added.

It is well within the ordinary skill of one practicing in the art to determine the effective amount of biocide for a given system or aqueous product being treated based on various parameters including but not limited to the size of the system, the pH, the types of organisms present and the amount of control desired.

Likewise, an effective amount of a synergistic combination of DBDCB and parabens should be applied to the article of manufacture being treated. Generally, a solution of the synergistic antimicrobial combination described above having a concentration of at least 0.1 ppm is incorporated into, sprayed onto, used to dip, or otherwise applied to the substrate being treated in order to prevent growth of bacteria, fungi, yeast and algae. Again, it is well within the ordinary skill of one practicing in the art to determine the effective amount of biocide to apply to a given article of manufacture being treated.

The active ingredients of the synergistic antimicrobial compositions of the present invention may be used in diverse formulations: solid, including finely divided powders and granular materials; as well as liquid, such as solutions, emulsions, suspensions, concentrates, emulsifiable concentrates, slurries and the like, depending upon the application intended, and the formulation media desired. Further, when the synergistic antimicrobial combinations are liquid, they may be employed neat or may be incorporated into various formulations, both solid and liquid, as an adsorbate on suitable inert carriers such as talc, clays, diatomaceous earth and the like, or water and various organic liquids such as lower alkanols, kerosene, benzene, toluene, and other petroleum distillate fractions or mixtures thereof. Glycols and phenoxyethanol are the preferred carriers. DBDCB is commercially available in wet cake, dry powder, and aqueous dispersion form from Calgon Corporation, Pittsburgh, Pa. Esters of parahydroxybenzoic acid are commercially available in powder form from Protameen Chemicals, Totowa, N.J.

It will also be understood by one skilled in the art that the synergistic antimicrobial combinations disclosed herein may be used in combination with other antimicrobial materials. For example, the combination can be combined with other fungicides and bactericides in appropriate concentrations and in appropriate instances so as to combine the action of each to obtain particularly useful results. Such combinations might find particular application in the preparation of germicidal soaps, in the production of cosmetics and aqueous coatings and in combating paper mill slime accumulations. It is quite clear also that the synergistic antimicrobial combinations of the present invention can be combined with other algicidal agents as well.

In accordance with the present invention there is still further provided a method of inhibiting the growth of at least one of: bacteria, yeast, fungi and algae. According to the methods of the present invention, this growth is inhibited in aqueous systems or on articles of manufacture prone to such growth. These methods comprise adding to the aqueous system or treating the article containing said bacteria, yeast, fungi and/or algae with an effective amount of a synergistic combination of DBDCB and one or more parabens. This addition can be accomplished either by simple addition of DBDCB and parabens together as a single admixture, or by addition of the two components separately. Such separate administration can either be at the same time or at different times. The net effect will be the same—the system or article being treated will ultimately have incorporated therein or have applied thereto the desired dosage concentration of each component.

Further, the compositions of the present invention are believed to be effective irrespective of the method of application. For example, the antimicrobial compositions described herein can be added to a system being treated via a low level, continuous feed practice, a semi-continuous feed practice or through slug feeding. All of these feeding practices will be familiar to one having ordinary skill in the art. Slug feeding is particularly effective and therefore is a preferred manner of employing the methods of the present invention. This type of feed allows the user to monitor the microorganism concentration in the system and feed product only when microorganism concentrations increase. The user realizes a cost savings by feeding an effective amount of DBDCB and parabens only when needed.

As noted above, the present invention is based upon the discovery that use of DBDCB in conjunction with parabens produces synergistic results and is effective in controlling the growth of bacteria, yeast, fungi and algae in a variety of industrial and other applications. The utility of the synergistic antimicrobial combination disclosed herein derives from its versatility both in the numerous industries in which it can be applied, as well as the numerous microorganisms against which it is effective. In particular, the large economic losses in papermaking operations caused by the accumulation of bacterial and fungal slimes in various parts of the system can be eliminated to a significant extent by use of the synergistic combination described herein.

The superior antimicrobial activity of the synergistic combination of DBDCB and parabens has been confirmed using standard laboratory techniques. In addition, the methods and combinations disclosed herein have been found to have a broad spectrum of biocidal efficacy. The combination of the present invention has been found effective, for example, in inhibiting bacterial growth including but not limited to *Klebsiella pneumoniae*, *Pseudomonas aeruginosa* and *Staphylococcus aureus*. The composition disclosed herein has also been found effective in inhibiting growth of fungi including but not limited to *Candida albicans*, white yeast, pink yeast, *Penicillium pinophilum*, and *Aspergillus niger*.

EXAMPLES

The following examples are set forth to illustrate the present invention and should not be construed as limiting the invention in any way.

Example I

The following example shows the biocidal efficacy and synergy in a microtiter test of the antimicrobial composition of the present invention against bacteria. Specifically, the antimicrobial composition as used in this example comprised DBDCB and methyl paraben. The two different bacterial strains used in the example are as follows:

| | |
|---|---|
| *Klebsiella pneumoniae* | ATCC 4352 |
| *Pseudomanas aeruginosa* | ATCC 15442 |

Each of the two bacteria were separately grown on Tryptone Glucose Extract (TGE) plates and incubated at 37° C. for a period of about 24 hours. The bacteria were then swabbed from their respective TGE plates and suspended in 10 ml of sterile phosphate buffer. A 0.5 McFarland turbidity standard, which will be familiar to one having ordinary skill in the art, was prepared in this manner for each of the two organisms. Each of the 10 ml organism suspensions were then diluted in a ratio of 1:10 with double strength Trypticase Soy Broth (2XTSB). The 2XTSB was prepared by adding 60 grams (g) of TSB powder into 1000 ml water and sterilizing by autoclaving at 121° C. for 15 minutes. Samples from each of these diluted cultures were then used as the inoculum for the microtiter tests.

An 8X stock solution of DBDCB having an 6400 parts per million (ppm) active concentration was prepared by dissolving about 0.64 g of about 100% active DBDCB in about 5 ml of methanol and diluting to about 100 ml with deionized water. The DBDCB used in the example was obtained from Calgon Corporation, Pittsburgh, Pa., Lot No. T2097P01. A 4X stock solution of methyl paraben having an active ingredient concentration of 4800 ppm was prepared by adding about 0.48 g of methyl paraben to about 100 ml of deionized water. The methyl paraben was obtained from Protameen Chemicals, Totowa, N.J., Lot No. 1759. About 0.4 g methyl paraben were added to about 100 ml deionized water to prepare a stock solution having an active concentration of 4000 ppm. About 0.32 g methyl paraben were added to about 100 ml deionized water to prepare a stock solution having an active concentration of 3200 ppm. About 0.24 g methyl paraben were added to about 100 ml deionized water to prepare a solution having an active concentration of about 2400 ppm. About 0.16 g of methyl paraben were added to about 100 ml deionized water to prepare a solution having an active concentration of 1600 ppm. About 50 ml of the 1600 ppm solution were added to about 50 ml deionized water to prepare a solution having an active concentration of 800 ppm. This 800 ppm solution then was subject to a serial dilution, using about 50 ml of the stock solution and about 50 ml deionized water to prepare stock solutions having active concentrations, in ppm, of 400, 200, 100, and 50. Prior to use, all of the methyl paraben stock solutions were heated to approximately 80° C. to dissolve the methyl paraben. These stock solutions were then cooled to about 37° C. before being used in the microtiter test.

Four sets of two microtiter plates each were used in the example. Each microtiter plate in the set had eight rows, A–H, and twelve columns, 1–12. Of the four sets, two sets were used to determine the minimum inhibitory concentration (MIC) of each biocide combination against each bacterial strain and two sets were used to determine the minimum biocidal concentration (MBC). The MIC is the lowest concentration of biocide that results in no evidence of growth at the end of a predetermined incubation period; here, that incubation period was 24 hours at 37° C. The MBC is the lowest concentration of biocide that results in no growth after subculturing and subsequent incubation; here, the subculturing occurred after 24 hours and the subcultured organisms incubated for an additional 24 hours at 37° C. "Growth" as used herein is defined as a turbidity or button of cells at the bottom of the well.

The final amount of each biocide in each well of the microtiter plates of each set used to determine MIC is depicted below in Tables 1 and 2. The amount of biocide in each well of the first microtiter plate in each set is as follows:

TABLE 1

AMOUNT OF EACH BIOCIDE IN WELLS OF FIRST MICROTITER PLATE IN EACH SET

| ROW LETTER | BIOCIDE | COLUMN CONCENTRATIONS (ppm Active) | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| A | DBDCB | 800 | 800 | 800 | 800 | 800 | 800 | 800 | 800 | 800 | 800 | 800 | — |
| | Paraben | 1200 | 1200 | 1000 | 1000 | 800 | 800 | 600 | 600 | 400 | 400 | 0 | — |
| B | DBDCB | 400 | 400 | 400 | 400 | 400 | 400 | 400 | 400 | 400 | 400 | 400 | — |
| | Paraben | 1200 | 1200 | 1000 | 1000 | 800 | 800 | 600 | 600 | 400 | 400 | 0 | — |
| C | DBDCB | 200 | 200 | 200 | 200 | 200 | 200 | 200 | 200 | 200 | 200 | 200 | — |
| | Paraben | 1200 | 1200 | 1000 | 1000 | 800 | 800 | 600 | 600 | 400 | 400 | 0 | — |
| D | DBDCB | 100 | 100 | 100 | 100 | 100 | 100 | 100 | 100 | 100 | 100 | 100 | — |
| | Paraben | 1200 | 1200 | 1000 | 1000 | 800 | 800 | 600 | 600 | 400 | 400 | 0 | — |
| E | DBDCB | 50 | 50 | 50 | 50 | 50 | 50 | 50 | 50 | 50 | 50 | 50 | — |
| | Paraben | 1200 | 1200 | 1000 | 1000 | 800 | 800 | 600 | 600 | 400 | 400 | 0 | — |
| F | DBDCB | 25 | 25 | 25 | 25 | 25 | 25 | 25 | 25 | 25 | 25 | 25 | — |
| | Paraben | 1200 | 1200 | 1000 | 1000 | 800 | 800 | 600 | 600 | 400 | 400 | 0 | — |
| G | DBDCB | 12.5 | 12.5 | 12.5 | 12.5 | 12.5 | 12.5 | 12.5 | 12.5 | 12.5 | 12.5 | 12.5 | — |
| | Paraben | 1200 | 1200 | 1000 | 1000 | 800 | 800 | 600 | 600 | 400 | 400 | 0 | — |
| H | DBDCB | 0 | 0 | 0 | 0 | 0 | 0 | 0 | 0 | 0 | 0 | 0 | — |
| | Paraben | 1200 | 1200 | 1000 | 1000 | 800 | 800 | 600 | 600 | 400 | 400 | 0 | — |

The amount of biocide in each well of the second microtiter plate in each set is as follows:

TABLE 2

AMOUNT OF EACH BIOCIDE IN WELLS OF SECOND MICROTITER PLATE IN EACH SET

| ROW LETTER | BIOCIDE | COLUMN CONCENTRATIONS (ppm Active) | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| A | DBDCB | 800 | 800 | 800 | 800 | 800 | 800 | 800 | 800 | 800 | 800 | 800 | — |
| | Paraben | 200 | 200 | 100 | 100 | 50 | 50 | 25 | 25 | 12.5 | 12.5 | 0 | — |
| B | DBDCB | 400 | 400 | 400 | 400 | 400 | 400 | 400 | 400 | 400 | 400 | 400 | — |
| | Paraben | 200 | 200 | 100 | 100 | 50 | 50 | 25 | 25 | 12.5 | 12.5 | 0 | — |
| C | DBDCB | 200 | 200 | 200 | 200 | 200 | 200 | 200 | 200 | 200 | 200 | 200 | — |
| | Paraben | 200 | 200 | 100 | 100 | 50 | 50 | 25 | 25 | 12.5 | 12.5 | 0 | — |
| D | DBDCB | 100 | 100 | 100 | 100 | 100 | 100 | 100 | 100 | 100 | 100 | 100 | — |
| | Paraben | 200 | 200 | 100 | 100 | 50 | 50 | 25 | 25 | 12.5 | 12.5 | 0 | — |
| E | DBDCB | 50 | 50 | 50 | 50 | 50 | 50 | 50 | 50 | 50 | 50 | 50 | — |
| | Paraben | 200 | 200 | 100 | 100 | 50 | 50 | 25 | 25 | 12.5 | 12.5 | 0 | — |
| F | DBDCB | 25 | 25 | 25 | 25 | 25 | 25 | 25 | 25 | 25 | 25 | 25 | — |
| | Paraben | 200 | 200 | 100 | 100 | 50 | 50 | 25 | 25 | 12.5 | 12.5 | 0 | — |
| G | DBDCB | 12.5 | 12.5 | 12.5 | 12.5 | 12.5 | 12.5 | 12.5 | 12.5 | 12.5 | 12.5 | 12.5 | — |
| | Paraben | 200 | 200 | 100 | 100 | 50 | 50 | 25 | 25 | 12.5 | 12.5 | 0 | — |

TABLE 2-continued

AMOUNT OF EACH BIOCIDE IN WELLS OF SECOND MICROTITER PLATE IN EACH SET

| ROW LETTER | BIOCIDE | COLUMN CONCENTRATIONS (ppm Active) | | | | | | | | | | | |
|---|---|---|---|---|---|---|---|---|---|---|---|---|
| | | 1 | 2 | 3 | 4 | 5 | 6 | 7 | 8 | 9 | 10 | 11 | 12 |
| H | DBDCB | 0 | 0 | 0 | 0 | 0 | 0 | 0 | 0 | 0 | 0 | 0 | — |
| | Paraben | 200 | 200 | 100 | 100 | 50 | 50 | 25 | 25 | 12.5 | 12.5 | 0 | — |

As is illustrated in the tables above, the amount of DBDCB added to the wells of rows A–H for each of the plates in the set was varied in a ladder series ranging from 800 ppm active to zero ppm active. The amount of paraben, in this case, methyl paraben, was similarly varied in columns 1–10 for both plates of the set in amounts ranging from 1200 ppm to zero ppm active paraben concentration. Column 11, rows A–G, for both plates of the set was used to determine the efficacy of DBDCB when used alone; likewise, row H, columns 1–10 of each plate of the set was used to determine the efficacy of methyl paraben when used alone. The wells corresponding with row H, column 11, of each plate in the set was the organism control, or positive control. That is, no biocide was added to these wells. This was done to ensure that the organisms were capable of growing in the environment provided. Column 12, rows A–H for each plate of the set represented a broth control, or a negative control. That is, no microorganisms were added to the wells of this column. This was done to ensure that there was no contamination of the plates.

The two sets of plates used to determine the MIC for each organism were set up as follows: 50 microliters of deionized water were added to all of the wells of both plates in each set. 50 microliters of 8X DBDCB stock solution were added the wells of row A, column 1–11. The contents of the row A wells containing the DBDCB 8X stock and water, were diluted down twofold to row G. That is, the contents of the row A, column 1 well were mixed, and 50 microliters of the mixture was transferred to the well of row B, column 1. This procedure was repeated down through row G and for each column. 50 microliters of the appropriate 4X methyl paraben stock solution were added to the wells as indicated in Tables 1 and 2 above. 50 microliters of deionized water were added to all of the wells in columns 11 and 12. 100 microliters of 2XTSB were added to all of the wells of column 12 for both plates in each set. 100 microliters of the appropriate organism suspension were added to all the wells in both plates of the set except the wells of column 12. The *Pseudomonas aeruginosa* was added to one set of two plates, and the *Klebsiella pneumoniae* was added to the other set of two plates. All four of these plates were then incubated at 37° C. for 24 hours.

Following this 24 hour incubation period, the two sets of microtiter plates used to determine the MBC were then set up. To the wells of the second two sets of plates were added 100 microliters of sterile 1XTSB. Ten microliters of the biocide/organism mixture were transferred from each well of the first two sets of plates to each respective well of the second two sets of plates. The second two sets of plates were then incubated at 37° C. for 24 hours.

Following the initial 24 hour incubation period for the MIC plates, and the subsequent 24 hour incubation period for the MBC plates, the presence or absence of growth in each well was determined. Growth in the microtiter plates was visually determined using a reading mirror, the use of which will be familiar to one having ordinary skill in the art. The presence or absence of growth in each well, along with the concentration of biocide in each well, was then used to determine the synergistic properties of the biocide combinations. The synergistic properties were evaluated by determining the Kull value, or K value; the K value was determined for each of the bacteria tested and for both the MIC and MBC plates. The method for calculating K value is well known to those skilled in the art. In all of the examples, the K value was determined by the following formula:

$$K = \frac{[DBDCB] \text{ In Combination}}{[DBDCB] \text{ Alone}} + \frac{[Paraben] \text{ In Combination}}{[Paraben] \text{ Alone}}$$

where "[DBDCB] In Combination" means the concentration of DBDCB which, when used in combination with one or more parabens, results in inhibition of microbial growth;

"[Paraben] In Combination" means the concentration of paraben used which, when used in combination with DBDCB, results in inhibition of microbial growth;

"[DBDCB] Alone" means the concentration of DBDCB which, when used alone, results in inhibition of microbial growth; and "[Paraben] Alone" means the concentration of paraben used which, when used alone, results in inhibition of microbial growth.

A K value of less than 1 indicates synergy between the two biocides, a K value of greater than 1 indicates antagonism between the two biocides, and a K value equal to 1 indicates an additive effect of the two biocides.

K values were determined for the organisms used in the example and are presented in Table 3.

TABLE 3

"K" VALUES OF DBDCB/METHYL PARABEN ADMIXTURE

| Organism | [DBDCB] Alone, ppm | [Methyl Paraben] Alone, ppm | [DBDCB] In Combination, ppm | [Methyl Paraben] In Combination, ppm | K Value | Weight Ratio |
|---|---|---|---|---|---|---|
| Pseudomonas aeruginosa | 400 | >1200 | 200 | 400 | <1 | 1:2 |
| Pseudomonas aeruginosa | 400 | >1200 | 100 | 800 | <1 | 1:8 |
| Pseudomonas aeruginosa | 400 | >1200 | 75 | 1200 | >1 | 1:16 |
| Pseudomonas aeruginosa | 400 | >1200 | 300 | 100 | <1 | 3:1 |
| Pseudomonas aeruginosa | 400 | >1200 | 300 | 25 | <1 | 12:1 |
| Pseudomonas aeruginosa | 400 | >1200 | 300 | 400 | >1 | 3:4 |
| Klebsiella pneumoniae | 50 | >1200 | 25 | 25 | <1 | 1:1 |
| Klebsiella pneumoniae | 50 | >1200 | 37.5 | 12.5 | <1 | 3:1 |
| Klebsiella pneumoniae | 37.5 | >1200 | 18.75 | 1200 | >1 | 1:64 |
| Klebsiella pneumoniae | 37.5 | >1200 | 37.5 | 800 | >1 | 1:21 |

In this Example, the concentration of methyl paraben alone needed to inhibit microbial growth exceeded test conditions, that is, was higher than 1200 ppm methyl paraben. Accordingly, the exact K value could not be determined. By assuming a methyl paraben concentration of at least 1200, since at least that much of the biocide alone is needed, K values of less than one are achieved; synergy was therefore demonstrated against both organisms tested.

Example II

The following example shows the biocidal efficacy and synergy in a microtiter test of the antimicrobial composition of the present invention against bacteria. Specifically, the antimicrobial composition as used in this example was comprised of DBDCB and propyl paraben. The same two bacterial strains used in Example I were tested against the biocide in Example II. The method of preparing the inoculum containing each of these bacterial strains was as described above for Example I.

An 8X DBDCB stock solution having an 6400 ppm active concentration was prepared by dissolving about 0.64 g of about 100% active DBDCB in about 5 ml of methanol and diluting with about 100 ml of deionized water. The DBDCB used in the example was obtained from Calgon Corporation, Pittsburgh, Pa., Lot No. T2097P01. Several 4X propyl paraben stock solutions, using propyl paraben obtained from Protameen Chemicals, Totowa, N.J., Lot No. 1764, were then prepared as follows: a stock solution having an active concentration of 8000 ppm was prepared by dissolving about 0.8 g propyl paraben in methanol and diluting to about 100 ml with deionized water; 50 ml of this 8000 ppm solution was then added to about 50 ml of deionized water to make a solution having an active concentration of 4000 ppm; a solution with an active concentration of 6000 ppm was prepared by dissolving about 0.6 g propyl paraben in about 5 ml methanol and diluting to about 100 ml with deionized water; 50 ml of the 6000 ppm solution was then mixed with about 50 ml deionized water to prepare a solution having an active concentration of 3000 ppm; a solution having an active concentration of 5000 ppm was prepared by dissolving about 0.5 g propyl paraben in about 5 ml methanol and diluting to about 100 ml with deionized water; a 2000 ppm solution was prepared by mixing about 50 ml of the 4000 ppm solution with about 50 ml deionized water; a 1000 ppm solution was prepared by mixing about 50 ml of the 2000 ppm solution with about 50 ml deionized water; a 400 ppm solution was prepared by dissolving about 0.04 g propyl paraben in about 5 ml methanol and diluting to about 100 ml with deionized water; a 200 ppm solution was prepared by adding 50 ml of the 400 ppm solution to about 50 ml of deionized water; and a 100 ppm solution was prepared by mixing about 50 ml of the 200 ppm solution with about 50 ml of deionized water.

The amount of biocide added to each well for both plates in each set is depicted below in Tables 4 and 5.

TABLE 4

AMOUNT OF EACH BIOCIDE IN WELLS OF FIRST MICROTITER PLATE IN EACH SET

| Row Letter | Biocide | COLUMN CONCENTRATIONS (ppm Active) | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| A | DBDCB | 800 | 800 | 800 | 800 | 800 | 800 | 800 | 800 | 800 | 800 | 800 | — |
| | Paraben | 2000 | 2000 | 1500 | 1500 | 1250 | 1250 | 1000 | 1000 | 750 | 750 | 0 | — |
| B | DBDCB | 400 | 400 | 400 | 400 | 400 | 400 | 400 | 400 | 400 | 400 | 400 | — |
| | Paraben | 2000 | 2000 | 1500 | 1500 | 1250 | 1250 | 1000 | 1000 | 750 | 750 | 0 | — |
| C | DBDCB | 200 | 200 | 200 | 200 | 200 | 200 | 200 | 200 | 200 | 200 | 200 | — |
| | Paraben | 2000 | 2000 | 1500 | 1500 | 1250 | 1250 | 1000 | 1000 | 750 | 750 | 0 | — |
| D | DBDCB | 100 | 100 | 100 | 100 | 100 | 100 | 100 | 100 | 100 | 100 | 100 | — |
| | Paraben | 2000 | 2000 | 1500 | 1500 | 1250 | 2500 | 1000 | 1000 | 750 | 750 | 0 | — |
| E | DBDCB | 50 | 50 | 50 | 50 | 50 | 50 | 50 | 50 | 50 | 50 | 50 | — |
| | Paraben | 2000 | 2000 | 1500 | 1500 | 1250 | 1250 | 1000 | 1000 | 750 | 750 | 0 | — |
| F | DBDCB | 25 | 25 | 25 | 25 | 25 | 25 | 25 | 25 | 25 | 25 | 25 | — |
| | Paraben | 2000 | 2000 | 1500 | 1500 | 1250 | 1250 | 1000 | 1000 | 750 | 750 | 0 | — |
| G | DBDCB | 12.5 | 12.5 | 12.5 | 12.5 | 12.5 | 12.5 | 12.5 | 12.5 | 12.5 | 12.5 | 12.5 | — |

TABLE 4-continued

AMOUNT OF EACH BIOCIDE IN WELLS OF FIRST MICROTITER PLATE IN EACH SET

| Row Letter | Biocide | COLUMN CONCENTRATIONS (ppm Active) | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| | Paraben | 2000 | 2000 | 1500 | 1500 | 1250 | 1250 | 1000 | 1000 | 750 | 750 | 0 | — |
| H | DBDCB | 0 | 0 | 0 | 0 | 0 | 0 | 0 | 0 | 0 | 0 | 0 | — |
| | Paraben | 2000 | 2000 | 1500 | 1500 | 1250 | 1250 | 1000 | 1000 | 750 | 750 | 0 | — |

TABLE 5

AMOUNT OF EACH BIOCIDE IN WELLS OF SECOND MICROTITER PLATE IN EACH SET

| ROW LETTER | BIOCIDE | COLUMN CONCENTRATIONS (ppm Active) | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| A | DBDCB | 800 | 800 | 800 | 800 | 800 | 800 | 800 | 800 | 800 | 800 | 800 | — |
| | Paraben | 500 | 500 | 250 | 250 | 100 | 100 | 50 | 50 | 25 | 25 | 0 | — |
| B | DBDCB | 400 | 400 | 400 | 400 | 400 | 400 | 400 | 400 | 400 | 400 | 400 | — |
| | Paraben | 500 | 500 | 250 | 250 | 100 | 100 | 50 | 50 | 25 | 25 | 0 | — |
| C | DBDCB | 200 | 200 | 200 | 200 | 200 | 200 | 200 | 200 | 200 | 200 | 200 | — |
| | Paraben | 500 | 500 | 250 | 250 | 100 | 100 | 50 | 50 | 25 | 25 | 0 | — |
| D | DBDCB | 100 | 100 | 100 | 100 | 100 | 100 | 100 | 100 | 100 | 100 | 100 | — |
| | Paraben | 500 | 500 | 250 | 250 | 100 | 100 | 50 | 50 | 25 | 25 | 0 | — |
| E | DBDCB | 50 | 50 | 50 | 50 | 50 | 50 | 50 | 50 | 50 | 50 | 50 | — |
| | Paraben | 500 | 500 | 250 | 250 | 100 | 100 | 50 | 50 | 25 | 25 | 0 | — |
| F | DBDCB | 25 | 25 | 25 | 25 | 25 | 25 | 25 | 25 | 25 | 25 | 25 | — |
| | Paraben | 500 | 500 | 250 | 250 | 100 | 100 | 50 | 50 | 25 | 25 | 0 | — |
| G | DBDCB | 12.5 | 12.5 | 12.5 | 12.5 | 12.5 | 12.5 | 12.5 | 12.5 | 12.5 | 12.5 | 12.5 | — |
| | Paraben | 500 | 500 | 250 | 250 | 100 | 100 | 50 | 50 | 25 | 25 | 0 | — |
| H | DBDCB | 0 | 0 | 0 | 0 | 0 | 0 | 0 | 0 | 0 | 0 | 0 | — |
| | Paraben | 500 | 500 | 250 | 250 | 100 | 100 | 50 | 50 | 25 | 25 | 0 | — |

The remaining test methods and conditions of Example II were carried out in the same manner as recorded in Example I. K values were determined for the organisms used in the example and are depicted below in Table 6.

TABLE 6

"K" VALUES OF DBDCB/PROPYL PARABEN ADMIXTURE

| Organism | [DBDCB] Alone, ppm | [Propyl Paraben] Alone, ppm | [DBDCB] In Combination, ppm | [Propyl Paraben] In Combination, ppm | K Value | Weight Ratio |
|---|---|---|---|---|---|---|
| Pseudomonas aeruginosa | 200 | 75 | 12.5 | 50 | 0.73 | 1:4 |
| Pseudomonas aeruginosa | 200 | 75 | 25 | 50 | 0.79 | 1:2 |
| Pseudomonas aeruginosa | 200 | 75 | 75 | 25 | 0.71 | 3:1 |
| Pseudomonas aeruginosa | 200 | 500 | 12.5 | 250 | 0.56 | 1:20 |
| Klebsiella pneumoniae | 50 | 250 | 18.75 | 100 | 0.78 | 1:53 |
| Klebsiella pneumoniae | 37.5 | 100 | 18.75 | 50 | 1.0 | 1:2.5 |

As can be seen from the results presented in Table 6, the synergy of DBDCB and propyl paraben was demonstrated against both *Pseudomonas aeruginosa* and *Klebsiella pneumoniae*.

Example III

The following example shows the biocidal efficacy and synergy in a microtiter test of the antimicrobial composition of the present invention against bacteria. Specifically, the antimicrobial composition as used in this example was comprised of DBDCB and butyl paraben. The three different bacterial strains used are indicated below:

| | |
|---|---|
| Pseudomonas aeruginosa | ATCC 15442 |
| Klebsiella pneumoniae | ATCC 4352 |
| Staphylococcus aureus | ATCC 6538 |

The bacterial inoculations were prepared as described above in Example I.

The stock solutions were prepared in the same manner as described for Example II; the butyl paraben was obtained from Protameen Chemicals, Totowa, N.J., Lot No. 1750. The biocides were added to three sets of two plates each, one set for each organism being tested, as indicated in Tables 4 and 5 above. K values were determined for each organism used in the example and are presented below in Table 7.

butyl paraben was obtained from Protameen Chemicals, Totowa, N.J., Lot No. 1750. The stock solutions were then added to each well of each plate. In this example, three sets of two plates each, one set for each organism, was used to

TABLE 7

"K" VALUES OF DBDCB/BUTYL PARABEN ADMIXTURE

| Organism | [DBDCB] Alone, ppm | [Butyl Paraben] Alone, ppm | [DBDCB] In Combination, ppm | [Butyl Paraben] In Combination, ppm | K Value | Weight Ratio |
|---|---|---|---|---|---|---|
| Pseudomonas aeruginosa | 200 | 75 | 150 | 25 | 1.08 | 6:1 |
| Pseudomonas aeruginosa | 200 | 75 | 100 | 25 | 0.83 | 4:1 |
| Pseudomonas aeruginosa | 200 | 75 | 25 | 50 | 0.79 | 1:2 |
| Pseudomonas aeruginosa | 300 | 500 | 25 | 250 | 0.58 | 1:10 |
| Pseudomonas aeruginosa | 300 | 500 | 100 | 100 | 0.53 | 1:1 |
| Pseudomonas aeruginosa | 300 | 500 | 200 | 25 | 0.72 | 8:1 |
| Klebsiella pneumoniae | 100 | 250 | 25 | 100 | 0.65 | 1:4 |
| Klebsiella pneumoniae | 100 | 250 | 50 | 50 | 0.70 | 1:1 |
| Klebsiella pneumoniae | 100 | 250 | 75 | 25 | 0.85 | 3:1 |
| Staphylococcus aureus | 25 | 250 | 12.5 | 50 | 0.70 | 1:4 |
| Staphylococcus aureus | 25 | 250 | 12.5 | 100 | 0.9 | 1:8 |
| Staphylococcus aureus | 25 | 250 | 6.25 | 100 | 0.65 | 1:16 |

As can be seen from the results in Table 7, synergy was demonstrated against all three of the bacterial strains tested.

Example IV

The following example shows the biocidal efficacy and synergy in a microtiter test of the antimicrobial composition of the present invention against fungi. Specifically, the antimicrobial composition used in this example was comprised of DBDCB and butyl paraben. Three different organisms were tested against the biocide, one yeast and two molds. The organisms used are as follows:

| Candida albicans | ATCC 10231 |
| Penicillium pinophilum | ATCC 9644 |
| Aspergillus niger | ATCC 9642 |

The inoculum containing the *Candida albicans* (yeast) was prepared by adding a swab of the organism to 100 ml of 2X Sabouraud Maltose Broth (2XSMB). The *Penicillium pinophilum* and *Aspergillus niger* (mold) inocula were prepared separately by adding 100 ml of 2XSMB to two bead bottles. A slant of each mold was scraped into each bead bottle and shaken to break up mycelia. The mold suspension was then filtered through angel hair to remove mycelial fragments, a process which is well known to those skilled in the art. The 2XSMB was prepared by adding 100 g of SMB powder to 1000 ml of deionized water and sterilized by autoclaving at 121° C. at 15 minutes.

DBDCB and butyl paraben stock solutions were prepared in the same manner as described above for Example II; the establish the MIC. Biocide was added to the wells as indicated in Tables 4 and 5 above.

The plates were set up as follows: 50 microliters of sterile deionized water were added to all of the wells. 50 microliters of the 8X DBDCB stock solution were added to the row A, columns 1–12 wells for plate 1, and the row A, columns 1–10 wells for plate 2. The DBDCB was diluted down twofold (50 microliters) through row G, in the same manner as explained above in Example 1. 50 microliters of the appropriate butyl paraben stock solution were added to the columns as indicated in Tables 4 and 5 above. 50 microliters of sterile deionized water were added to the wells of columns 9–12 in plate 2. 100 microliters of 2XSMB were added to the wells of columns 11 and 12 of plate 2. 100 microliters of each organism suspension were then added to each well of plate 1, and the rows A–H, columns 1–10 wells of plate 2. In this example, columns 11 and 12 of the second plate represented a negative control. That is, no microorganisms were added to the wells of this column. This was done to ensure that there was no contamination of the plates. Row H, columns 9 and 10 of the second plate represented a positive control. That is, the organisms were added but no biocide was added. This was done to ensure that the organisms were capable of growing in the environment provided.

The MIC plates were incubated at 30° C. for seven days. After 24 hours, the MBC subculture plates were prepared as described above in Example I. K values for the organisms were then determined and are presented in Table 8.

TABLE 8

"K" VALUES OF DBDCB/BUTYL PARABEN ADMIXTURE

| Organism | [DBDCB] Alone, ppm | [Butyl Paraben] Alone, ppm | [DBDCB] In Combination, ppm | [Butyl Paraben] In Combination, ppm | K Value | Weight Ratio |
|---|---|---|---|---|---|---|
| Candida albicans | 100 | 100 | 25 | 50 | 0.75 | 1:2 |
| Candida albicans | 100 | 250 | 50 | 50 | 0.70 | 1:1 |
| Candida albicans | 100 | 100 | 50 | 25 | 0.75 | 2:1 |
| Penicillium pinophilum | 25 | 100 | 12.5 | 50 | 1.0 | 1:4 |

TABLE 8-continued

"K" VALUES OF DBDCB/BUTYL PARABEN ADMIXTURE

| Organism | [DBDCB] Alone, ppm | [Butyl Paraben] Alone, ppm | [DBDCB] In Combination, ppm | [Butyl Paraben] In Combination, ppm | K Value | Weight Ratio |
|---|---|---|---|---|---|---|
| Penicillium pinophilum | 100 | 250 | 50 | 100 | 0.90 | 1:2 |
| Penicillium pinophilum | 100 | 250 | 50 | 50 | 0.70 | 1:1 |
| Aspergillus niger | 400 | 250 | 100 | 100 | 0.65 | 1:1 |
| Aspergillus niger | 400 | 250 | 100 | 50 | 0.45 | 2:1 |
| Aspergillus niger | 400 | 250 | 200 | 25 | 0.60 | 8:1 |

As can be seen from the results in Table 8, synergy was demonstrated against all three of the fungi tested.

Example V

The methods of Example IV were repeated but using propyl paraben rather than butyl paraben. K values are presented in Table 9.

TABLE 9

"K" VALUES OF DBDCB/PROPYL PARABEN ADMIXTURE

| Organism | [DBDCB] Alone, ppm | [Propyl Paraben] Alone, ppm | [DBDCB] In Combination, ppm | [Propyl Paraben] In Combination, ppm | K Value | Weight Ratio |
|---|---|---|---|---|---|---|
| Candida albicans | 100 | 250 | 25 | 100 | 0.65 | 1:4 |
| Candida albicans | 100 | 250 | 50 | 50 | 0.70 | 1:1 |
| Candida albicans | 100 | 250 | 50 | 25 | 0.60 | 2:1 |
| Candida albicans | 100 | 625 | 25 | 250 | 0.65 | 1:10 |
| Penicillium pinophilum | 50 | 100 | 12.5 | 50 | 0.75 | 1:4 |
| Penicillium pinophilum | 50 | 100 | 25 | 25 | 0.75 | 1:1 |
| Aspergillus niger | 400 | 250 | 200 | 50 | 0.70 | 4:1 |
| Aspergillus niger | 400 | 250 | 200 | 25 | 0.60 | 8:1 |
| Aspergillus niger | 200 | 875 | 50 | 250 | 0.54 | 1:5 |
| Aspergillus niger | 200 | 875 | 100 | 100 | 0.51 | 1:1 |

As can be seen from the results of Table 9, synergy was demonstrated against all three of the fungi tested.

What is claimed is:

1. A synergistic antimicrobial combination comprising:
   a) 1,2-dibromo-2,4-dicyanobutane; and
   b) at least one ester of parahydroxybenzoic acid selected from the group consisting of methyl paraben, ethyl paraben, propyl paraben, butyl paraben, isopropyl paraben, isobutyl paraben and benzyl paraben, wherein the weight ratio of a) to b) on an active basis ranges between about 12:1 and 1:20.

2. A method of inhibiting microbial growth in an aqueous system which comprises adding to said system an effective amount of a synergistic antimicrobial combination comprising:
   a) 1,2-dibromo-2,4-dicyanobutane; and
   b) at least one ester of parahydroxybenzoic acid selected from the group consisting of methyl paraben, ethyl paraben, propyl paraben, butyl paraben, isopropyl paraben, isobutyl paraben and benzyl paraben, wherein the weight ratio of a) to b) on an active basis ranges between about 12:1 and 1:20.

3. The method of claim 2 wherein the 1,2-dibromo-2,4-dicyanobutane and at least one ester of parahydroxybenzoic acid are added together as a single composition to the system being treated.

4. The method of claim 1 wherein the 1,2-dibromo-2,4-dicyanobutane and at least one ester of parahydroxybenzoic acid are added separately to the system being treated.

5. The method of claim 1 wherein at least 1 ppm of the synergistic antimicrobial composition is added to the system being treated.

6. The method of claim 1 wherein between about 1 ppm and 2000 ppm of the synergistic antimicrobial composition is added to the system being treated.

7. A method of inhibiting microbial growth on an article of manufacture which comprises applying to said article an effective amount of a synergistic antimicrobial combination comprising:
   a) 1,2-dibromo-2,4-dicyanobutane; and
   b) at least one ester of parahydroxybenzoic acid selected from the group consisting of methyl paraben, ethyl paraben, propyl paraben, butyl paraben, isopropyl paraben, isobutyl paraben and benzyl paraben, wherein the weight ratio of a) to b) on an active basis ranges between about 12:1 and 1:20.

8. The method of claim 7 wherein the 1,2-dibromo-2,4-dicyanobutane and at least one ester of parahydroxybenzoic acid are applied together as a single composition to the article being treated.

9. The method of claim 7 wherein the 1,2-dibromo-2,4-dicyanobutane and at least one ester of parahydroxybenzoic acid are applied separately to the article being treated.

10. The method of claim 9 wherein said synergistic antimicrobial composition has a concentration of at least 0.1 ppm.

* * * * *